(12) United States Patent
Blaustein et al.

(10) Patent No.: US 8,234,742 B2
(45) Date of Patent: Aug. 7, 2012

(54) COMPLEX MOTION TOOTHBRUSH

(75) Inventors: Lawrence A. Blaustein, Moreland Hills, OH (US); Douglas A. Gall, Strongsville, OH (US); Patrick W. Brown, Auburn, OH (US)

(73) Assignee: The Procter & Gamble Company, Cincinatti, OH (US)

( * ) Notice: Subject to any disclaimer, the term of this patent is extended or adjusted under 35 U.S.C. 154(b) by 0 days.

(21) Appl. No.: 12/636,863

(22) Filed: Dec. 14, 2009

(65) Prior Publication Data
US 2010/0088833 A1      Apr. 15, 2010

Related U.S. Application Data

(63) Continuation of application No. 11/358,582, filed on Feb. 21, 2006, now Pat. No. 7,761,947, which is a continuation of application No. 11/200,680, filed on Aug. 10, 2005, now abandoned, which is a continuation of application No. 10/903,222, filed on Jul. 30, 2004, now abandoned, which is a continuation of application No. 10/036,613, filed on Nov. 7, 2001, now abandoned.

(51) Int. Cl.
*A47L 9/04* (2006.01)

(52) U.S. Cl. .............. 15/167.1; 15/22.1; 15/22.4
(58) Field of Classification Search .............. 15/22.1, 15/22.2, 22.4, 167.1
See application file for complete search history.

(56) References Cited

U.S. PATENT DOCUMENTS

| | | | | |
|---|---|---|---|---|
| 3,196,299 A * | 7/1965 | Kott | ............. | 310/81 |
| 3,242,516 A * | 3/1966 | Cantor | ............. | 15/28 |
| 5,524,312 A * | 6/1996 | Tan et al. | ............. | 15/22.1 |
| 5,651,158 A * | 7/1997 | Halm | ............. | 15/167.1 |
| 5,956,797 A * | 9/1999 | Wilson | ............. | 15/167.1 |
| 6,178,582 B1 * | 1/2001 | Halm | ............. | 15/167.1 |
| 6,237,178 B1 * | 5/2001 | Krammer et al. | ............. | 15/22.1 |

* cited by examiner

*Primary Examiner* — Laura C Guidotti
(74) *Attorney, Agent, or Firm* — George Henry Leal; Vladimir Vitenberg

(57) ABSTRACT

A head for a toothbrush has a longitudinal axis and a transverse axis. The transverse axis is generally perpendicular to the longitudinal axis. The head includes a first cleaning element carrier and a second cleaning element carrier. The second cleaning element carrier is asymmetrically fixed to the head such that the second cleaning element carrier can move relative to the head about the transverse axis of the head.

6 Claims, 7 Drawing Sheets

COMPLEX MOTION TOOTHBRUSH

CROSS REFERENCES TO RELATED APPLICATIONS

This application is a continuation of application Ser. No. 11/358,582, filed on Feb. 21, 2006 now U.S. Pat. No. 7,761, 947, which is a continuation of application Ser. No. 11/200, 680, filed Aug. 10, 2005, now abandoned, which is a continuation of application Ser. No. 10/903,222, filed Jul. 30, 2004, now abandoned, which is a continuation of application Ser. No. 10/036,613, filed Nov. 7, 2001, now abandoned, the substances of which are incorporated herein by reference.

FIELD OF THE INVENTION

The invention is related to the art of toothbrushes

DESCRIPTION OF RELATED ART

The invention relates more particularly to electrically driven toothbrushes in which brush bristles are arranged to be moved relative to the toothbrush handle. There are many examples of such toothbrushes including the disclosure in 1939 of rotary driven bristles in U.S. Pat. No. 2,215,031, A similar rotational drive arrangement is also shown in U.S. Pat. Nos. 4,845,795, 4,156,620 explains how a rotational motor drive is converted into reciprocal linear motion to drive the bristles rotationally clockwise and counterclockwise, U.S. Pat. No. 3,577,579 discloses a toothbrush in which a toothbrush head is moved in relation to a brush holder so that all the bristles mounted in the brush head move together sideways and backwards and forwards relative to the holder. U.S. Pat. No. 5,625,916 discloses a toothbrush with a single bristle holder. The bristle holder is driven to vibrate in a rotational manner about a shaft. U.S. Pat. No. 5,617,603, the substance of which is hereby incorporated by reference, discloses a toothbrush with two bristle holders interconnected by a separate swing bar. The swing bar is mounted on a pivot pin. The two bristle holders include recesses, which receive ball ends of the swing bar.

The drive mechanisms and brush motions disclosed in these references range from the relatively simple to the relatively complex. The complex disclosures describe toothbrushes that provide elaborate brushing motions. However, the toothbrushes are far too complicated and involve too many moving parts to be a practical brushing solution in many applications. The simpler of the disclosed toothbrushes, provide only one brushing action. These singular brushing actions may provide adequate brushing action in some applications. However, they may also be inadequate in other brushing situations. For example, they may not adequately clean spaces between teeth.

It is desirable therefore to provide a toothbrush that is simple to manufacture, having few moving parts, while providing a plurality of cleaning or brushing actions for accomplishing a plurality of teeth cleaning tasks.

BRIEF SUMMARY OF THE INVENTION

The oral care device of the present invention can provide the user with a better oral health experience. In some embodiments, a head for a toothbrush has a longitudinal axis and a transverse axis, the transverse axis being generally perpendicular to the longitudinal axis. The head comprises a first cleaning element carrier and a second cleaning element carrier. The second cleaning element carrier is asymmetrically fixed to the head such that the second cleaning element carrier can move relative to the head about the transverse axis of the head.

In other embodiments, a toothbrush comprises a handle and a head connected to the handle. The head includes a first cleaning element carrier, a second cleaning element carrier, an upstanding head portion, and a resilient biasing member. The first cleaning element carrier and the second cleaning element carrier are separated by a gap. The second cleaning element carrier is disposed nearer to the handle than the first cleaning element carrier. The upstanding head portion is disposed nearer to the handle than the second cleaning element carrier.

The resilient biasing member is mounted between the upstanding head portion and a side of the second cleaning element carrier. The resilient biasing member is positioned such that the resilient biasing member urges the second cleaning element carrier toward the first cleaning element carrier.

In other embodiments, a toothbrush comprises a handle and a head connected to the handle. The head comprises a first cleaning element carrier, a second cleaning element carrier, an upstanding head portion, and a resilient biasing member. The first cleaning element carrier and the second cleaning element carrier are separated by a gap. The second cleaning element carrier is disposed nearer to the handle than the first cleaning element carrier. The second cleaning element carrier is fixed to the head such that the second cleaning element carrier can pivot symmetrically relative to the head. The upstanding head portion is disposed nearer to the handle than the second cleaning element carrier. The resilient biasing member is mounted between the upstanding head portion and a side of the second cleaning element carrier.

BRIEF DESCRIPTION OF THE SEVERAL VIEWS OF THE DRAWINGS

The invention may take form in various components and arrangements of components, and in various procedures and arrangements of procedures. The drawings are only for purposes of illustrating preferred embodiments, they are not to scale, and are not to be construed as limiting the invention.

DETAILED DESCRIPTION OF THE INVENTION

Figure 1:
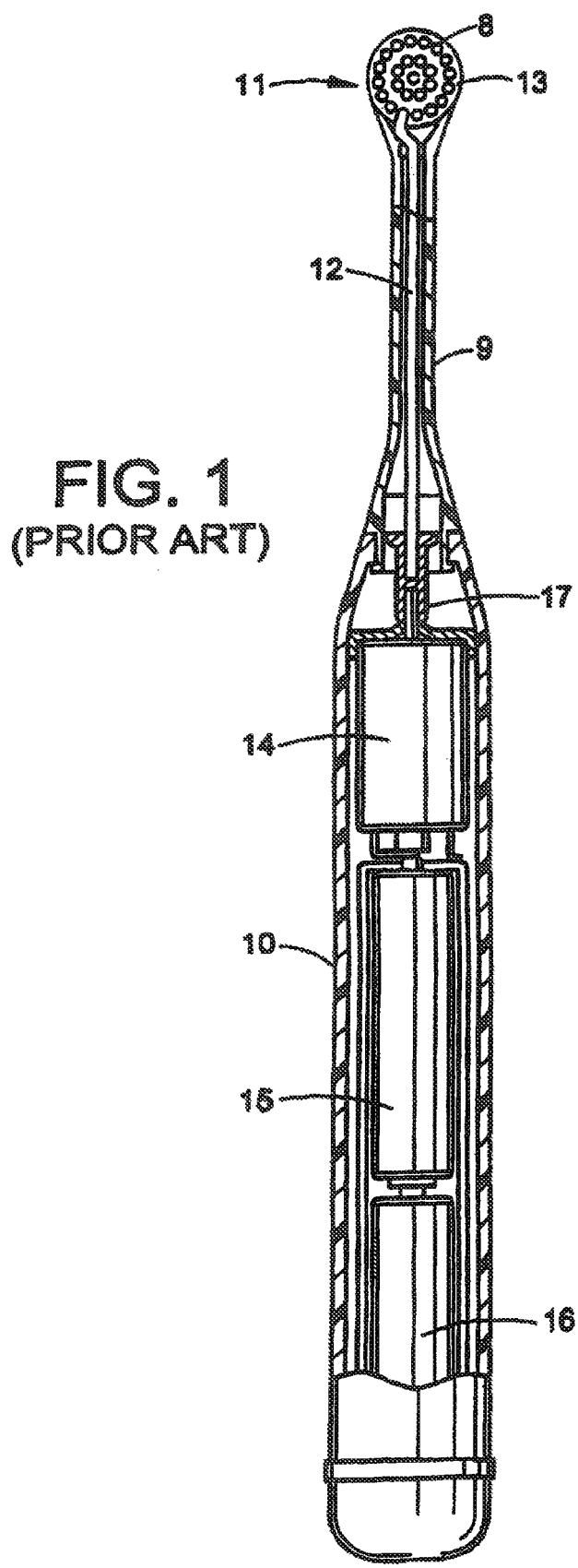
FIG. 1 is a sectional bottom view of a prior art toothbrush.
Figure 4:
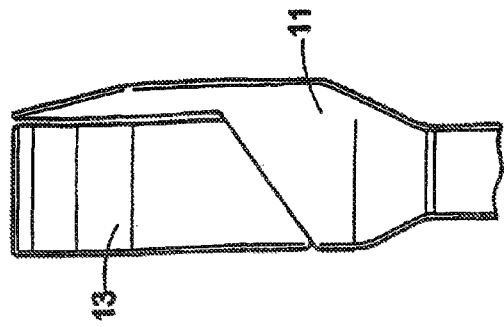
FIG. 4 is an opposite side view of FIG. 2.
Figure 7:
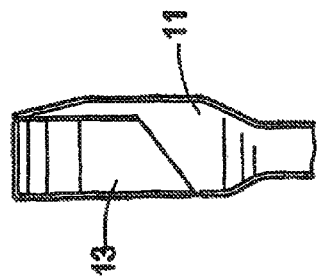
FIGS. 5, 6 and 7 are respectively the same views as FIGS. 2, 3 and 4 of a different prior art toothbrush and to a different scale.

Referring to the drawings, in FIG. 1 the toothbrush comprises a handle portion 10 at a first end of the toothbrush, a head section 11 at a second end of the toothbrush, a neck 9 extending therebetween, a rotatable shaft 12 extending from the handle to the head, and a generally circular bristle holder 13 having a plurality of bristle tufts embedded therein, wherein each tuft 8 comprises a plurality of bristles. The handle provides compartments for holding an electric motor 14 and two batteries 15 and 16, although a rechargeable power source can be substituted for the batteries 15 and 16. A shaft coupling 17 is arranged to grip one end of the shaft 12 and allow the shaft to be pulled out for cleaning or replacement as will be described below.

Figure 2:
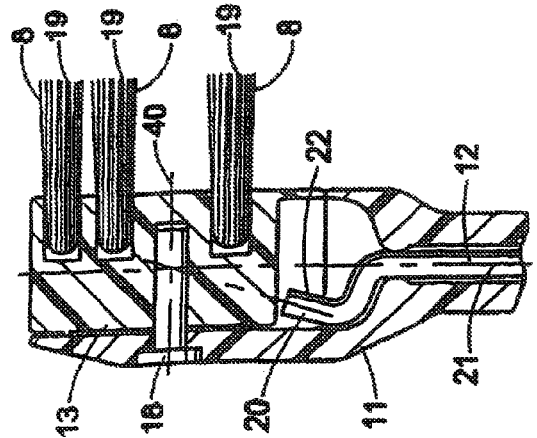
FIG. 2 shows a cross-sectional side view of part of the prior art toothbrush.

The head 11, as is better seen in FIG. 2, supports a post 18, which provides a rotational or oscillatory pivot axis 40 for the bristle holder 13. Bristles 19 are shown for illustrative purposes only in FIG. 2. The shaft 12 has an integrally formed remote-most end, gear tooth or gear tooth 20 that is off-set from a central longitudinal axis 21 of the shaft. The remotemost end, gear tooth or cam 20 fits into a slot 22 (see FIG. 3) formed in a side of the bristle holder 13. It will be noted that the end 20 points towards an intersection of the first axis 21 and the pivot axis 40 of the post 18. In one embodiment, the post is arranged so that the pivot axis 40 is substantially perpendicular to the central longitudinal axis 21 of the shaft. The pivot axis 40 is also substantially parallel to the central longitudinal axis 21 of the shaft. The pivot axis 40 is also substantially parallel to the direction in which the bristles 19 extend. While this arrangement is preferred, it is contemplated that the post 18 can be arranged differently. For example, the post 18 might be angled so that the pivot axis 40 is not substantially perpendicular to the longitudinal axis 21 of the shat but rather forms an acute angel therewith in order to provide a wobbling or swiveling action about the pivot axis 40. When the shaft 12 is rotated by the motor 14, the remote end, gear tooth or cam 20 describes a circle about the shaft 12 and drivingly engages the slot 22 to cause the bristle holder 13 to vibrate or oscillate about the pivot axis of the bristle holder 13. In this regard the remote end is formed into a remote gear tooth or cam 20. As may be seen in FIG. 3, slot 22 is closed-ended and extends radially inward from the outer circumference of the holder to less than the distance to the center of the holder and between adjacent pairs of bristle holes. Thus, the bristle holder 13 pivots, oscillates, or rotates forwards and backwards about the center of the post 18. Such movement provides a first relative motion between the head 11 and the bristles 19 and is generally beneficial for efficient cleaning of teeth. The width of the slot 22 is preferably generally the same as the diameter of the end 20 to leave minimum play; this keeps noise to a minimum in use.

Figure 5:
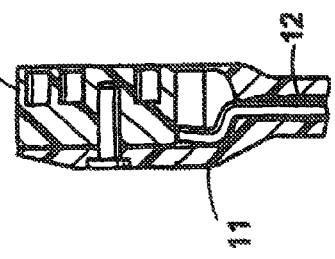
Figure 8:
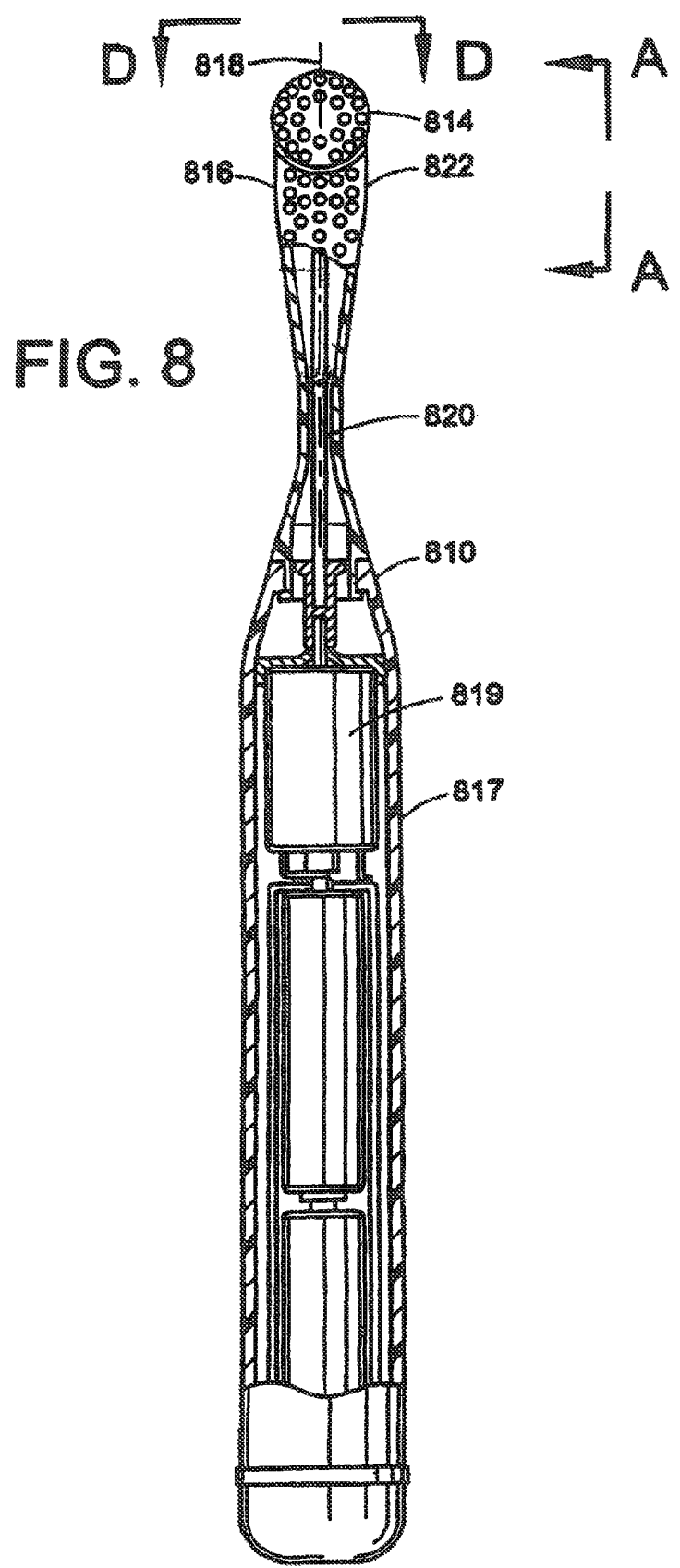
FIG. 8 is a bottom view of an enhanced toothbrush in partial section.

Preferably, the motor 14 runs at around 6000 rpm. Where desired, the motor can run at other speeds or be arranged to run at two or more speeds, selectable by the user. FIG. 1 shows a toothbrush where the holder 13 vibrates, oscillates or rotates through an angle of 30 degrees. In FIG. 2, the angle is 35 degrees and in FIG. 5 the angle is 15 degrees. It will therefore be appreciated that the rotational angle can be chosen by fitting different shafts 12 and that the same bristle holder can be used for all angles.

Figure 3:
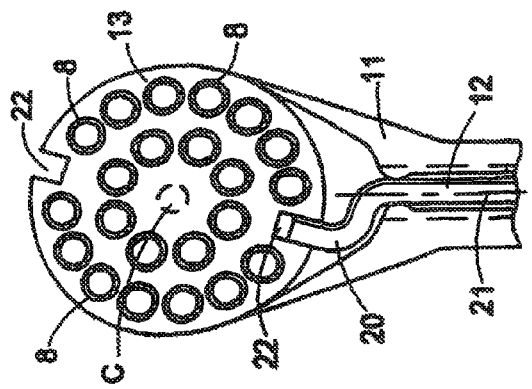
FIG. 3 is a sectional bottom view of FIG. 2.
Figure 6:
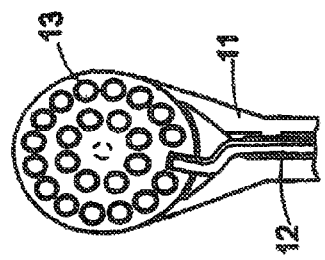

Each bristle holder 13 may be provided with more than one slot 22 as may be seen in FIG. 3, opposite each other so as to be better balanced or so that different slots can be used if the one slot wears or if the bristles wear unevenly in use. In other words, the holder 13 can then be set up in two or more rotational positions. The holder 13 is preferable easily removable from the head 11, by being spring clipped to the post 18, for example. Such removal allows better cleaning and storing in a hygienic container perhaps and also enables the shaft 12 to be readily withdrawn and replaced when required.

The described shafts 12 are preferably integrally formed, i.e., a single length of a thin rod and shaped as shown. However, it is possible to arrange for the remote end or cam 20 to be separately formed or provided and fixed to a part of the shaft. Such a separate part can be a brush having a central axis coinciding with the axis 21 of the shaft and an off-center driving post. The driving post then takes up the position and function of the remote cam 20. Thus, the driving post and the slot 22 then form the driving engagement between the shaft and the holder 13 and so the driving post can be regarded as the remote cam of the shaft.

It is also possible, but not usually so convenient, in some embodiments of the invention to arrange for the holder 13 to be hingedly pivoted at one side, for example opposite the shaft. In such a case, bristles mounted nearer the hinged pivot will not actually move as much as bristles at the side next to the shaft but they will still vibrate significantly.

It will also be appreciated that whether pivoted to rotate or to hinge, the bristle holder 13 need not be circular. However, a circular holder 13 is normally preferred so that its rotational position can be changed when desired, as mentioned above.

While the above-described shaft arrangement is preferred, it is contemplated that other shaft arrangements can be used with the present invention. For example, the arrangement described in U.S. Pat. No. 5,732,432, the substance of which is incorporated herein by reference, might be substituted to accommodate mechanical misalignments of the shaft and mechanical strain during use. Further, the head 11 might be provided in a form in which it can be readily detached from the handle 10. This could be accomplished using, coupling arrangements for the shaft and body portion of the head. Such arrangements are known in the art. For example, the head and handle portions can include mating slots, spring clips, and protrusions and/or locking or securing tabs and grooves. The shaft can be divided into two sections, each section including a coupling element. For example, the coupling is achieved with a keyed arrangement. For instance, coupling elements can include male and female mating splines affixed to respective shaft section ends, or as shown in U.S. Pat. No. 5,617,601, the substance of which is incorporated herein by reference. Further, the slot 22 might be replaced by a wobble plate, such as described in U.S. Pat. No. 5,764,743, the substance of which is incorporated herein by reference.

With additional reference now to FIG. 8-FIG. 15, embodiments of an enhanced electric toothbrush 810 include a first bristle holder 814 similar to the bristle holder 13 described above. The enhanced toothbrush 810 has a head portion 816 and a body or handle portion 817. Of course, the enhanced toothbrush includes a motor 819 and batteries for powering the motor. The head portion 816 has a longitudinal axis 818.

The first bristle holder 814 is illustrated as circular. However, other shape bristle holders are contemplated and within the scope of the invention. The first bristle holder 814 includes at least one slot described above for receiving a remote most end or cam of a driving shaft 820 as described in reference to FIG. 1-FIG. 7. The remote-most cam (see FIG. 3) of the driving shaft is bent or offset from a central longitudinal axis 21 (see FIG. 3) of the driving shaft 820 as described above. In short, with regard to the construction and operation of the shaft 820 in relation to the first bristle holder 814, the enhanced toothbrush 810 is similar to the toothbrush described in reference to FIG. 1-FIG. 7. However, embodiments of the enhanced electric toothbrush 810 also include second bristle holders, such as second bristle holder 822. While it is desirable to locate the second bristle holder directly adjacent the first bristle holder, it is contemplated that a gap 1830 (shown in FIG. 18) may be provided between the first and second bristle holders. In addition, the space between the movable first and second bristle holders might be filled with stationary or fixed bristles which are embedded in fixed or stationary third bristle holder 1814 (shown in FIG. 18) which forms part of the toothbrush head. In many embodiments of the enhanced electric toothbrush, the second bristle holders are movable and separately associated with, and separately driven by, a driving shaft such as the driving shaft 820. The movable second bristle holders are movable in directions and/or manners that are different and distinct from whichever of the rotary or hingedly pivoted vibratory movements, described in reference to FIG. 1-FIG. 7, is used in the particular embodiment.

Figure 9:
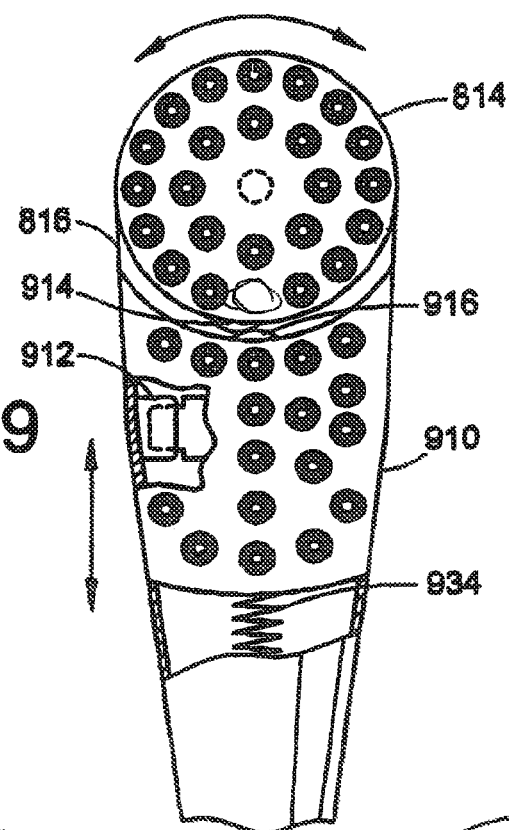
FIG. 9 is a bottom view, in partial section, of a first embodiment of a head portion of the enhanced toothbrush of FIG. 8.

For example, referring to FIG. 9, a second bristle holder 910 is movably mounted in slots 912 in the toothbrush head 816 and driven in a vibratory, longitudinal motion by the motion of the first bristle holder 814. For example, the first bristle holder 814 includes a cam 914. The second bristle holder includes a cam follower 916. The cam 914 and cam follower 916 are generally disposed in opposing relation. Additionally, depending on the position of the first bristle holder 814, the cam 914 and cam follower 916 can be in an engaged relation. The cam and cam follower 914, 916 can comprise molded protrusions on the first 814 and second 910 bristle holders respectively. The cam and cam follower 914, 916 are rigidly mounted to or within the first 814 and second 910 bristle holders. That is to say, the cam and cam follower 914, 916 do not move significantly with regard to their respective bristle holders. Therefore the cam and cam follower 914, 916 do not constitute additional moving parts. As the motor 819 of the enhanced toothbrush 810 rotates the shaft 820, a remote-most cam of the shaft 820 (not shown, but similar to 20 of FIG. 3) drives the first bristle holder into rotational vibratory motion as described above in reference to FIG. 1-FIG. 7. As the first bristle holder vibrates or oscillates the first cam 914 comes into contact with a surface of the second cam or cam follower 916 and drives the cam follower 916, and therefore, the second bristle holder in a longitudinal direction along the longitudinal axis 818 of the head portion 816. As the shaft 918 continues to rotate, the first cam 914 becomes disengaged with the cam follower 916. A resilient biasing member such as a spring 934, lodged or mounted, for example, between a wall 1820 (shown in FIG. 18) of the head portion 816 and a surface 1818 (shown in FIG. 18) of the second bristle holder 910, urges the second bristle holder 910 back toward the first bristle holder 814. As this back and forth or up and down motion (relative to the figure) is repeated (as the shaft 820 continues to rotate), a brushing motion is provided that is distinct from and complimentary to the circular motion provided by the first bristle holder 814.

Figure 10:
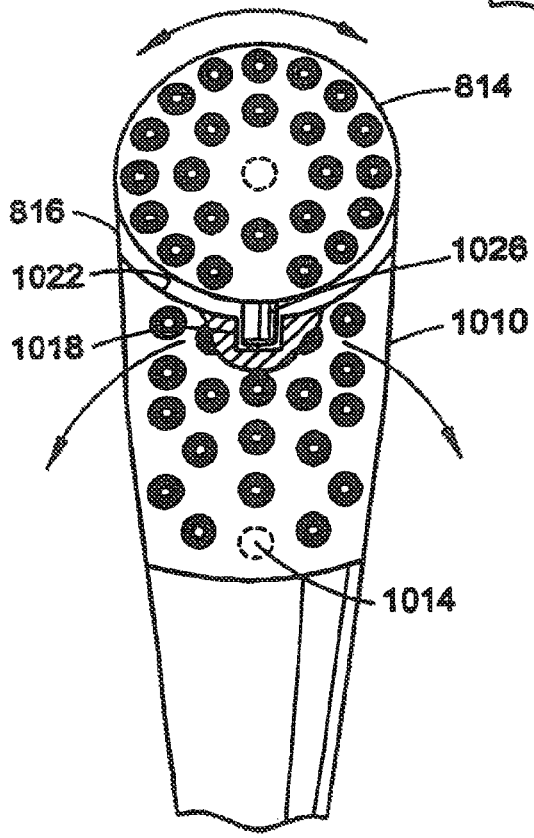
FIG. 10 is a bottom view, in partial section, of a second embodiment of a head portion of the enhanced toothbrush of FIG. 8.

Referring to FIG. 10, in a second embodiment of the enhanced toothbrush 810 a second bristle holder 1010 is movably mounted the toothbrush head 816 and driven in a vibratory, swinging, oscillating or pivoting motion about a hinge or pivot 1014, by the first bristle holder 814. The second bristle holder 1010 is longitudinally spaced from the first bristle holder 814. A first side 1018 of the second bristle holder 1010 faces the first bristle holder 814. The first side 1018 includes a slot 1022. The pivot or hinge 1014 is offset from a center of the second bristle holder. For example, the pivot 1014 is located at a side spaced, or remote from, the first side 1018. A pin 1026 interconnects the first bristle holder 814 with the second bristle holder 1010. Preferably, the pin 1026 is molded into, and unitary with, the first bristle holder 814. The pin 1026 is rigidly mounted to or within the first 814 holder. That is to say, the pin 1026 does not move significantly with respect to the first bristle holder. Therefore, the pin 1026 does not constitute an additional moving part. The pin 1026 is received in the slot 1022 in the second bristle holder 1010. The slot 1022 is sized to allow the pin 1018 to slide and pivot relative to the slot and to engage portions of walls of the slot. As the motor 819 of the enhanced toothbrush 810 rotates the shaft 820, a remote-most end or cam (not shown, but similar to 20 of FIG. 3) of the shaft 820 drives the first bristle holder 814 into rotational vibratory motion as described above in reference to FIG. 1-FIG. 7. As the first bristle holder 814, vibrates or oscillates, the pin 1018 associated therewith is sweeps out and arc. As the pin 1026 sweeps out the arc in a first direction, the pin 1026 engages a first wall of the slot 1022 and urges the first wall, and therefore, the second bristle holder, to move in the first direction. Since the movement of the second bristle holder is constrained by the hinge or pivot 1014, the second bristle holder 1010 is made to swing about the pivot in the first direction. As the shaft 820 continues to rotate, the first bristle holder is made to move in a second direction. Therefore the pin 1026 is made to sweep out an arc in the second direction. As the pin 1026 sweeps out the arc in the second direction, the pin 1026 engages a second wall of the slot 1022 and urges the second wall, and therefore the second bristle holder, to move in the second direction. Since the movement of the second bristle holder is constrained by the hinge or pivot 1014, the second bristle holder 1010 is made to swing about the pivot in the second direction. As this swinging or pivoting motion is repeated (as the shaft 818 continues to rotate), a brushing motion is provided that is complimentary to that provided by the first bristle holder 814. For example, as the first bristle holder rotates clockwise, the second bristle holder pivots in a complimentary counter clockwise direction.

Figure 11:
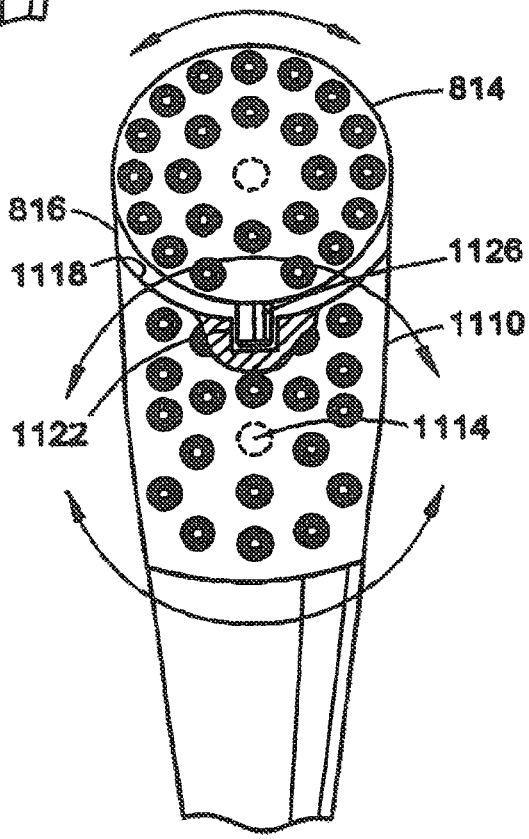
FIG. 11 is a bottom view, in partial section, of a third embodiment of a head portion of the enhanced toothbrush of FIG. 8.

Referring to FIG. 11, in a third embodiment of the enhanced toothbrush 810 a second bristle holder 1110 is movably mounted the toothbrush head 816 and driven in a vibratory, swinging, oscillating or pivoting motion about a pivot 1114, by the first bristle holder 814. The second bristle holder 1110 is longitudinally spaced from the first bristle holder 814. A first side 1118 of the second bristle holder 1110 faces the first bristle holder 814. The first side 1118 includes a slot 1122. The pivot 1114 is centrally located within the second bristle holder. A pin 1126 interconnects the first bristle holder 814 with the second bristle holder 1110. Preferably, the pin 1126 is molded into, and unitary with, the first bristle holder 814. The pin 1126 is rigidly mounted to or within the first bristle holder 814. That is to say, the pin 1126 does not move significantly with respect to the first bristle holder 814. Therefore, the pin 1126 does not constitute an additional moving part. The pin 1126 is received in the slot 1122 in the second bristle holder 1110. The slot 1122 is sized to allow the pin 1126 to slide and pivot relative to the slot and to engage portions of walls of the slot 1122. As the motor 819 of the enhanced toothbrush 810 rotates the shaft 820, a remote-most cam (not shown, but similar to 20 of FIG. 3) of the shaft 820 drives the first bristle holder into rotational or pivotal vibratory motion as described above in reference to FIG. 1-FIG. 7. As the first bristle holder 814 vibrates, the pin 1118 associated therewith is sweeps out an arc. As the pin 1126 sweeps out the arc in a first direction, the pin 1126 engages a first wall of the slot 1122 and urges the first wall, and therefore the second bristle holder to move in the first direction. Since the movement of the second bristle holder is constrained by the pivot 1114, the second bristle holder 1110 is made to swing or rotate about the pivot 1114 in the first direction. As the shaft 820 continues to rotate, the first bristle holder is made to move in a second direction.

Therefore the pin 1126 is made to sweep out an arc in the second direction. As the pin 1126 sweeps out the arc in the second direction, the pin 1126 engages a second wall of the slot 1122 and urges the second wall, and therefore the second bristle holder 1110 to move in the second direction. Since the movement of the second bristle holder is constrained by the pivot 1114, the second bristle holder 1110 is made to swing or rotate about the pivot in the second direction. As this swinging or pivoting motion is repeated (as the shaft 820 continues to rotate), a brushing motion is provided that is complimentary to that provided by the first bristle holder 814. For example, as the first bristle holder moves clockwise, the second bristle holder moves in a complimentary counter clockwise direction.

Figure 12:
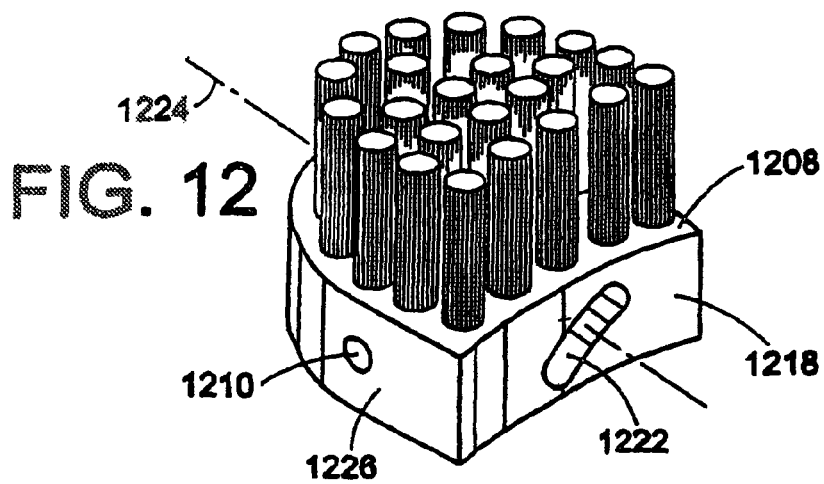
FIG. 12 is an orthographic view of a second bristle holder of a fourth embodiment of a head portion of the enhanced toothbrush of FIG. 8.
Figure 13:
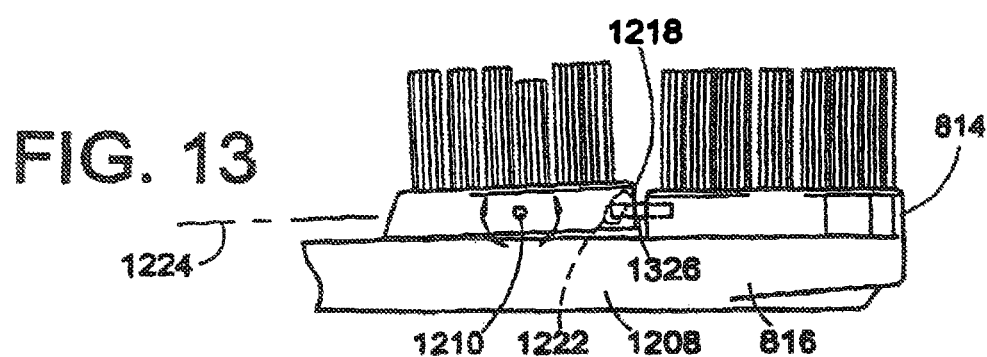
FIG. 13 is a side view, taken along A-A of FIG. 8, in partial section of the fourth embodiment of a head portion of the enhanced toothbrush of FIG. 8.

Referring to FIG. 12 and FIG. 13, in a fourth embodiment of the enhanced toothbrush 810, a second bristle holder 1208 is movably mounted to the toothbrush head 816 with a pivot 1210 installed at a centrally located transverse axis of the second bristle holder 1208. The second bristle holder 1208 is driven in a vibratory, swinging or teetering motion by the first bristle holder 814. The second bristle holder 1208 is longitudinally spaced from the first bristle holder 814. A first side 1218 of the second bristle holder 1208 faces the first bristle holder 814. The first side 1218 includes a slot 1222. The slot is disposed transversely to a longitudinal axis 1224 of the second bristle holder 1208 and is oriented at an angle to a plane defined by a base 1226 of the second bristle holder 1208. A pin 1326 interconnects the first bristle holder 814 with the second bristle holder 1208. Preferably, the pin 1326 is molded into, and unitary with, the first bristle holder 814. The pin 1326 is rigidly mounted to or within the first 814 bristle holder. That is to say, the pin 1326 does not move significantly with respect to the first bristle holder. Therefore, the pin 1326 does not constitute an additional moving part. The pin 1326 is received in the angled slot 1222 in the second bristle holder 1208. The slot 1222 is sized to allow the pin 1326 to slide and swing relative to the slot and to engage portions of walls of the slot. As the motor 819 of the enhanced toothbrush 810 rotates the shaft 820, a remote-most end or cam of the shaft 820 (not shown, but similar to 20 of FIG. 3) drives the first bristle holder into rotational or pivotal oscillatory or vibratory motion as described above in reference to FIG. 1-FIG. 7. As the first bristle holder 814 vibrates, the pin 1326 associated therewith, sweeps out an arc. As the pin 1326 sweeps out the arc in a first direction, the pin 1326 engages a first or for example, upper wall of the slot 1222 and urges the first wall, and therefore the second bristle holder, to move in the first or for example, upward (relative to the figure) direction. Since the movement of the second bristle holder is constrained by the pivot 1210, the second bristle holder 1110 is made to swing, teeter or rotate about the pivot 1210 in the first, or for example, upward direction. As the shaft 820 continues to rotate, the first bristle holder is made to move in a second direction. Therefore the pin 1326 is made to sweep out an arc in the second direction. As the pin 1326 sweeps out the arc in the second direction, the pin 1326 engages a second, or for example, lower (relative to the figure) wall of the slot 1222 and urges the second wall, and therefore the second bristle holder 1208 to move in the second, or for example, lower, direction (relative to the figure). Since the movement of the second bristle holder is constrained by the pivot 1210, the second bristle holder 1208 is made to swing, rotate, or teeter about the pivot 1210 in the second direction. As this swinging, pivoting or teetering motion is repeated (as the shaft 820 continues to rotate), a flossing or deep cleaning motion is provided that is distinct from, and complimentary to, the oscillating motion provided by the first bristle holder 814.

Figure 14:
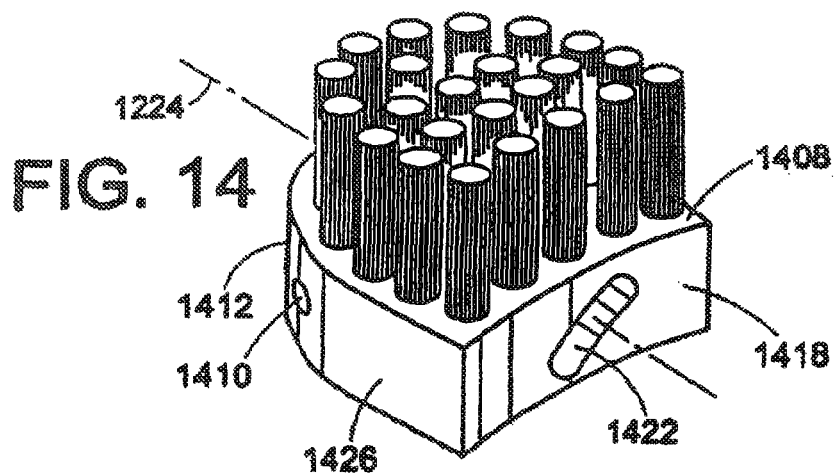
FIG. 14 is an orthographic view of a second bristle holder of a fifth embodiment of a head portion of the enhanced toothbrush of FIG. 8.
Figure 15:
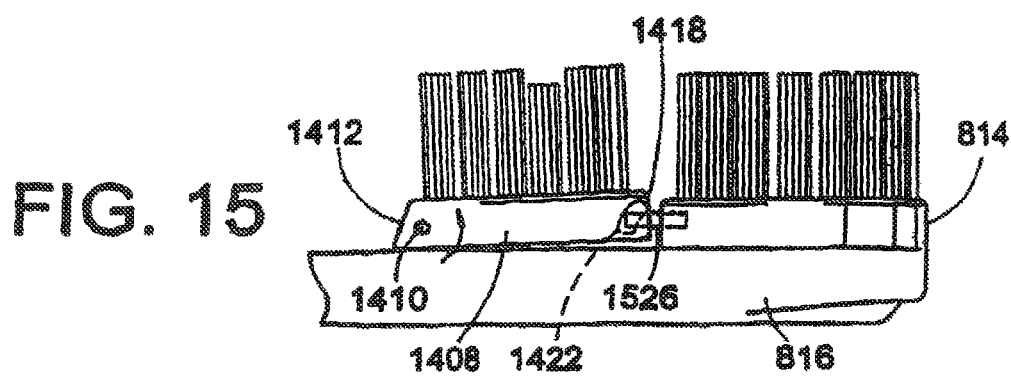
FIG. 15 is a side view, taken along A-A of FIG. 8, in partial section of the fifth embodiment of a head portion of the enhanced toothbrush of FIG. 8.
Figure 18:
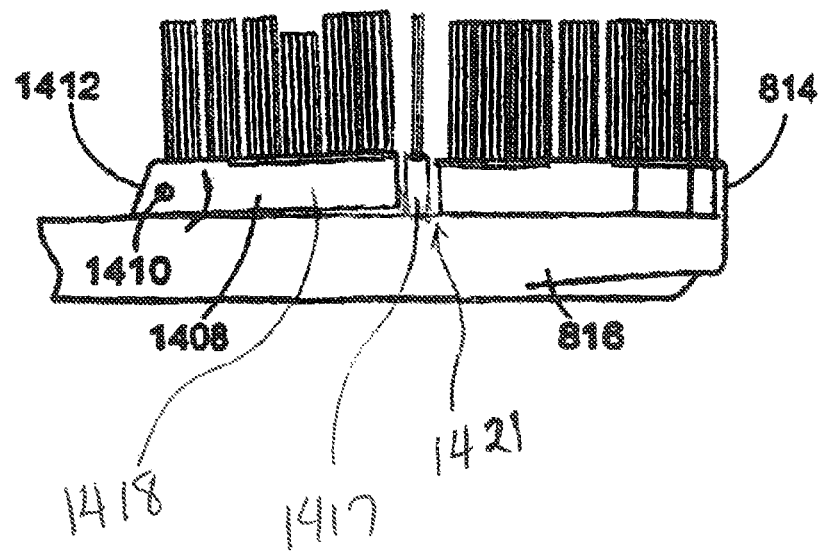
FIG. 18 is a side view showing another embodiment of the present invention.

Referring to FIG. 14 and FIG. 15, in a fifth embodiment of the enhanced toothbrush 810, a second bristle holder 1408 is movably mounted to the toothbrush head 816 with a pivot 1410 installed at a transverse axis of the second bristle holder 1408 located adjacent to a proximal end 1412 of the second bristle holder 1410. The second bristle holder 1408 is driven in a vibratory, swinging or teetering motion by the first bristle holder 814. The second bristle holder 1408 is longitudinally spaced from the first bristle holder 814. A first side 1418 of the second bristle holder 1408 faces the first bristle holder 814. The first side 1418 includes a slot 1422. The slot is disposed transversely to a longitudinal axis 1424 of the second bristle holder 1408 and is oriented at an angle to a plane defined by a base 1426 of the second bristle holder 1408. A pin 1526 interconnects the first bristle holder 814 with the second bristle holder 1408. Preferably, the pin 1526 is molded into, and unitary with, the first bristle holder 814. The pin 1526 is rigidly mounted to or within the first 814 holders. That is to say, the pin 1526 does not move significantly with respect to the first bristle holders. Therefore, the pin 1526 does not constitute an additional moving part. The pin 1326 is received in the angled slot 1422 in the second bristle holder 1208. The slot 1422 is sized to allow the pin 1526 to slide and swing relative to the slot and to engage portions of walls of the slot. As the motor 819 of the enhanced toothbrush 810 rotates the shaft 820, a remote-most cam (not shown, but similar to 20 of FIG. 3) of the shaft 820 drives the first bristle 814 holder into rotational or pivotal vibratory motion as described above in reference to FIG. 1-FIG. 7. As the first bristle holder 814 vibrates, the pin 1526 associated therewith, sweeps out an arc. As the pin 1526 sweeps out the arc in a first direction, the pin 1526 engages a first or, for example, upper wall of the slot 1222 and urges the first wall, and therefore the second bristle holder, to move in a first, or for example, an upward (relative to the figure) direction. Since the movement of the second bristle holder is constrained by the pivot 1410, the second bristle holder 1110 is made to swing, or orbit about the pivot 1410 in the first, or for example, upward direction. As the shaft 820 continues to rotate, the first bristle holder is made to move in a second direction. Therefore the pin 1526 is made to sweep out an arc in a second direction. As the pin 1526 sweeps out the arc in the second direction, the pin 1326 engages a second, or for example, lower (relative to the figure) wall of the slot 1422 and urges the second wall, and therefore the second bristle holder 1408 to move in the second, or for example, lower, direction. Since the movement of the second bristle holder is constrained by the pivot 1410, the second bristle holder 1408 is made to swing, or orbit about the pivot 1410 in the second direction. As this swinging, or orbiting motion is repeated (as the shaft 820 continues to rotate), a flossing or deep cleaning motion is provided that is distinct from, and complimentary to, the oscillating motion provided by the first bristle holder 814. Referring to FIG. 18, while it is desirable to locate the second bristle holder 1408 directly adjacent the first bristle holder 814, it is contemplated that a gap 1421 may be provided between the first and second bristle holders 814, 1408, respectively. In addition, the space between the movable first and second bristle holders might be filled with stationary or fixed bristles which are embedded in fixed or stationary third bristle holder 1417 which forms part of the toothbrush head.

Figure 16:
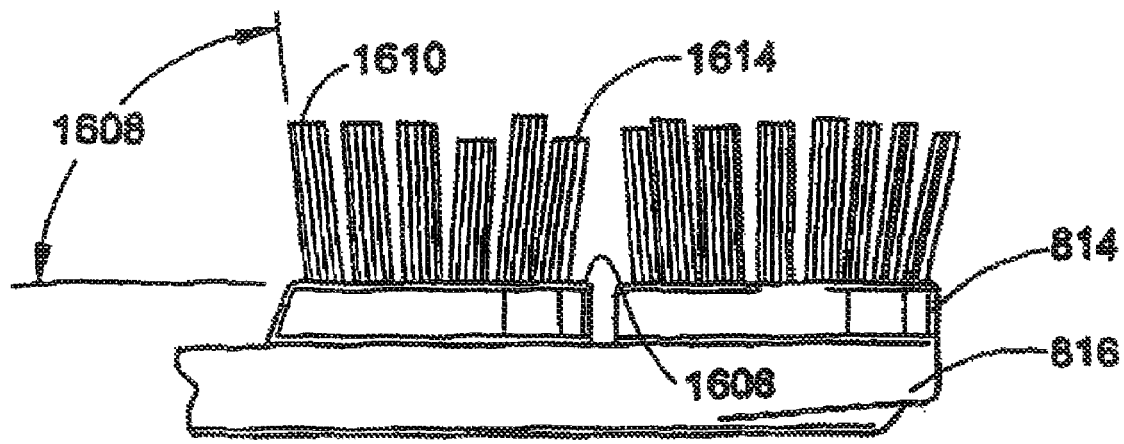
FIG. 16 is a side view of a toothbrush showing a first exemplary alternate bristle arrangement.
Figure 17:
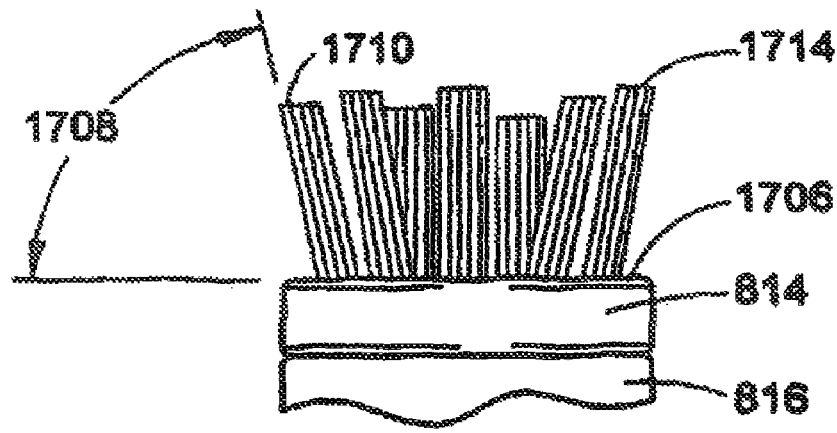
FIG. 17 is an end view taken along D-D of FIG. 8 showing a second exemplary bristle arrangement.

While the embodiments of the present invention have been illustrated for simplicity with bristles, which extend in a direction substantially perpendicular to the longitudinal axis 818 and the surface of the bristle holders, it is contemplated that the bristles might be arranged differently to complement or further enhance the motions of the first and/or second bristle holders. For example, referring to FIG. 16, some or all of the bristles might extend in a direction which forms an acute angle 1608 to a surface 1606 of the bristle holder and extends in a direction toward or away from the handle, such as shown by way of example with respect to bristles 1610 and 1614 respectively. Referring to FIG. 17, in another embodiment, some of the bristles might extend outwardly away from head, in another direction, again forming an acute angle 1708 with respect to a surface 1706 of the bristle holder, as shown by way of example with respect to bristles 1710 and 1714. Massaging bristles or bristles of varying height might also be used, such as described in U.S. Pat. Nos. Des. 330,286, Des. 434,563, the substances of which are incorporated herein by reference. Other preferred bristle arrangements suitable for use include those arrangements described in whole or part in U.S Pat. Nos. 6,006,394; 4,081,876; 5,046,213; 5,335,389; 5,392,483; 5,446,940; 4,894,880; and international publication no. WO 99/23910; the substances of which are incorporated herein by reference.

The described embodiments have been described with certain words and phrases that attempt to describe certain motions. Motion can either be constant or vibratory. One example of a constant motion is simple rotation where an element angularly moves in a single direction (e.g., a bristle holder which only rotates clockwise or swivels clockwise in a cone like envelope) or translates in a single direction. Vibration is any periodic movement having repeated cycles. Vibratory motion can have one or more frequencies and amplitudes. Vibratory movement which is substantially linear is referred to herein as a reciprocating motion. Reciprocating motion can occur in a number of directions, such as substantially horizontal, substantially vertical (i.e., a lifting or pulsating motion), and combinations thereof. Vibratory movement which is substantially rotational in nature is referred to herein as an oscillatory or pivoting motion.

Because most motions can be complex in nature (i.e., include elements of other types of motion), the use of the above-described terms herein can include other motions, unless stated otherwise (e.g., reciprocates only), in addition to the basic or primary motion described by the term. So, for example, a motion which is described herein as reciprocating may also include other vibratory or constant movements even though the primary movement is reciprocatory in nature.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

The invention has been described with reference to particular embodiments. Modifications and alterations will occur to others upon reading and understanding this specification. For example, while the first bristle holder has been described and illustrated as being adjacent a remote-most end of the toothbrush and the second bristle holder as being located more proximally, the two holders may be switched in position. For example, the first, or driven, bristle holder may be located proximally while the second or slave bristle holder is located at the remote or more distal end of the toothbrush. While the pins have been described as being molded unitary components of the first bristle holder, the pins may comprise separately manufactured and subsequently fixedly attached, inserted or co-molded components. It is intended that all such modifications and alterations are included insofar as they come within the scope of the appended claims or equivalents thereof.

What is claimed is:

1. A head for a toothbrush having a longitudinal axis and a transverse axis, the transverse axis being generally perpendicular to the longitudinal axis, the head comprising:
   a proximal end and a distal end;
   a top surface; and
   a first cleaning element carrier and a second cleaning element carrier, the second cleaning element carrier having a fixed end and a free end, the free end being spaced from the proximal end and the distal end of the head, the second cleaning element carrier being asymmetrically fixed to the head such that the second cleaning element carrier can move relative to the head about the transverse axis of the head such that the free end of the second cleaning element carrier moves to and from the top surface. and wherein when the free end is moved from the top surface, the free end is superjacent to the top surface, wherein the second cleaning element carrier includes a slot, and
   wherein a portion of the first cleaning element carrier is disposed within the slot.

2. The toothbrush of claim 1, wherein the free end is disposed adjacent to the first cleaning element carrier and the fixed end is disposed opposite the free end.

3. The toothbrush head of claim 1, wherein the second cleaning element carrier is driven in a vibratory motion.

4. A head for a toothbrush having a longitudinal axis and a transverse axis, the transverse axis being generally perpendicular to the longitudinal axis, the head comprising:
   a proximal end and a distal end;
   a top surface; and
   a first cleaning element carrier and a second cleaning element carrier, the second cleaning element carrier having a fixed end and a free end, the free end being spaced from the proximal end and the distal end of the head, the second cleaning element carrier being asymmetrically fixed to the head such that the second cleaning element carrier can move relative to the head about the transverse axis of the head such that the free end of the second cleaning element carrier moves to and from the top surface, and wherein when the free end is moved from the top surface, the free end is superjacent to the top surface, wherein a gap exists between the first cleaning element carrier and the second cleaning element carrier, and wherein a third cleaning element carrier is disposed within the gap.

5. The toothbrush of claim 4, wherein the third cleaning element carrier is stationary.

6. A toothbrush comprising:
a handle;
a head connected to the handle, wherein the head includes a first cleaning element carrier and a second cleaning element carrier, the first cleaning element carrier and the second cleaning element carrier being separated by a gap, the second cleaning element carrier being disposed nearer to the handle than the first cleaning element carrier, the second cleaning element carrier having a plurality of cleaning elements extending therefrom the second cleaning element carrier having a longitudinal axis and a transverse axis, the transverse axis being generally perpendicular to both the longitudinal axis and a general direction in which the plurality of cleaning elements extends, the second cleaning element carrier being fixed to the head such that the second cleaning element carrier can pivot symmetrically relative to the head about the transverse axis;
a wall being disposed nearer to the handle than the second cleaning element carrier; and
a resilient biasing member mounted between the wall and a side of the second cleaning element carrier.

* * * * *